(12) United States Patent
Babiarz et al.

(10) Patent No.: US 10,092,479 B2
(45) Date of Patent: Oct. 9, 2018

(54) MUSCLE AND TISSUE THERAPY DEVICE

(71) Applicant: KOREEXTREME LLC, Chicago, IL (US)

(72) Inventors: Shawn Babiarz, Chicago, IL (US); Matthew Gelber, Champaign, IL (US)

(73) Assignee: KOREEXTREME LLC, Chicago, IL (US)

( * ) Notice: Subject to any disclaimer, the term of this patent is extended or adjusted under 35 U.S.C. 154(b) by 564 days.

(21) Appl. No.: 14/651,128

(22) PCT Filed: Dec. 10, 2013

(86) PCT No.: PCT/US2013/074089
§ 371 (c)(1),
(2) Date: Jun. 10, 2015

(87) PCT Pub. No.: WO2014/093324
PCT Pub. Date: Jun. 19, 2014

(65) Prior Publication Data
US 2015/0313789 A1    Nov. 5, 2015

Related U.S. Application Data

(60) Provisional application No. 61/736,589, filed on Dec. 13, 2012.

(51) Int. Cl.
*A61H 1/00* (2006.01)
*A61H 1/02* (2006.01)
(Continued)

(52) U.S. Cl.
CPC ............ *A61H 15/00* (2013.01); *A61F 7/02* (2013.01); *A61H 15/0092* (2013.01);
(Continued)

(58) Field of Classification Search
CPC .... A61H 15/00; A61H 15/0092; A61H 15/02; A61H 2201/0228; A61H 2201/0214;
(Continued)

(56) References Cited

U.S. PATENT DOCUMENTS 1,581,248 A * 4/1926 Thompson ......... A61H 15/0092
                                                    601/120
2,104,429 A * 1/1938 Lipsner .............. A61H 15/0092
                                                    601/118
(Continued)

FOREIGN PATENT DOCUMENTS

WO    1994021211 A1    9/1994
WO    1998046187 A1    10/1998
(Continued)

*Primary Examiner* — Garrett Atkinson
(74) *Attorney, Agent, or Firm* — Valauskas Corder LLC

(57) ABSTRACT

A massage therapy device having a roller and detachable thermal cover is disclosed. The roller has a series of unique ridges that optimize the application of therapeutic pressure to portions of a user's body. The thermal cover contains thermal retention material that can be heated or cooled. When the thermal cover is detachably connected to the roller, thermal therapy can be applied to muscle and other tissue in conjunction with the pressure therapy applied with the ridges of the roller. The configuration, temperature, and pressure application angle of the device can be varied to maximize the versatility of the device and provide individualized treatment.

20 Claims, 12 Drawing Sheets

(51) Int. Cl.
*A61H 5/00* (2006.01)
*A61H 15/00* (2006.01)
*A61H 15/02* (2006.01)
*A61F 7/02* (2006.01)
*A61F 7/03* (2006.01)

(52) U.S. Cl.
CPC ............. *A61H 15/02* (2013.01); *A61F 7/034* (2013.01); *A61F 2007/0207* (2013.01); *A61F 2007/0285* (2013.01); *A61H 2015/0014* (2013.01); *A61H 2201/0207* (2013.01); *A61H 2201/0214* (2013.01); *A61H 2201/0228* (2013.01); *A61H 2201/0257* (2013.01); *A61H 2201/0278* (2013.01); *A61H 2201/1284* (2013.01)

(58) Field of Classification Search
CPC .... A61H 2201/0257; A61H 2201/1284; A61H 2201/0278; A61H 2015/0014; A61H 2201/0207; A61F 7/02; A61F 2007/0207; A61F 7/034
See application file for complete search history.

(56) References Cited

U.S. PATENT DOCUMENTS

| | | | | |
|---|---|---|---|---|
| 2,446,099 | A * | 7/1948 | Niblack | A61H 15/0078 601/127 |
| 4,014,325 | A * | 3/1977 | Clarke | A61H 15/00 601/121 |
| 4,884,560 | A * | 12/1989 | Kuracina | A61H 15/0092 601/19 |
| 4,945,900 | A * | 8/1990 | Masuda | A61H 15/0092 601/120 |
| 5,025,777 | A * | 6/1991 | Hardwick | A61F 7/034 126/204 |
| 5,478,988 | A * | 12/1995 | Hughes | A47J 36/2494 165/46 |
| 6,129,687 | A * | 10/2000 | Powell | A61H 15/02 220/4.07 |
| 6,398,694 | B1 * | 6/2002 | Bountourakis | A63B 21/015 482/109 |
| 6,648,904 | B2 * | 11/2003 | Altshuler | A46B 15/0036 492/46 |
| 6,793,636 | B1 * | 9/2004 | Pepera | A61F 7/02 601/121 |
| 7,112,178 | B1 * | 9/2006 | Roozenburg | A61H 1/0266 601/121 |
| 7,811,216 | B2 * | 10/2010 | Babiarz | A63B 21/00069 446/220 |
| 9,107,795 | B2 * | 8/2015 | Faussett | A61H 15/0092 |
| 9,463,133 | B2 * | 10/2016 | Rodgers | A61H 7/00 |
| 2008/0200851 | A1 * | 8/2008 | Faussett | A61H 15/0092 601/119 |
| 2009/0112137 | A1 * | 4/2009 | Lamore | A63B 21/0004 601/112 |
| 2011/0077665 | A1 * | 3/2011 | Tittas | A45D 26/0061 606/133 |
| 2011/0245741 | A1 * | 10/2011 | L'Homme | A61H 15/0085 601/120 |
| 2012/0035029 | A1 * | 2/2012 | Dye | A61H 15/0092 482/132 |
| 2012/0209154 | A1 * | 8/2012 | Williams, III | A61F 7/02 601/19 |
| 2012/0209363 | A1 * | 8/2012 | Williams, III | A61F 7/02 607/114 |
| 2012/0265106 | A1 * | 10/2012 | Accardo | A61H 15/0092 601/15 |
| 2013/0085426 | A1 * | 4/2013 | Brodsky | A61H 15/00 601/128 |
| 2013/0184620 | A1 * | 7/2013 | Cohen | A61H 15/0092 601/118 |
| 2013/0245509 | A1 * | 9/2013 | Tanigawa | A61H 15/0092 601/20 |
| 2016/0310352 | A1 * | 10/2016 | Chen | A61H 15/02 |
| 2017/0216130 | A1 * | 8/2017 | Jones | A61H 15/00 |

FOREIGN PATENT DOCUMENTS

| | | | | |
|---|---|---|---|---|
| WO | | 2004058132 A1 | 7/2004 | |
| WO | WO | 2004058132 A1 * | 7/2004 | ......... A61H 15/0092 |

* cited by examiner

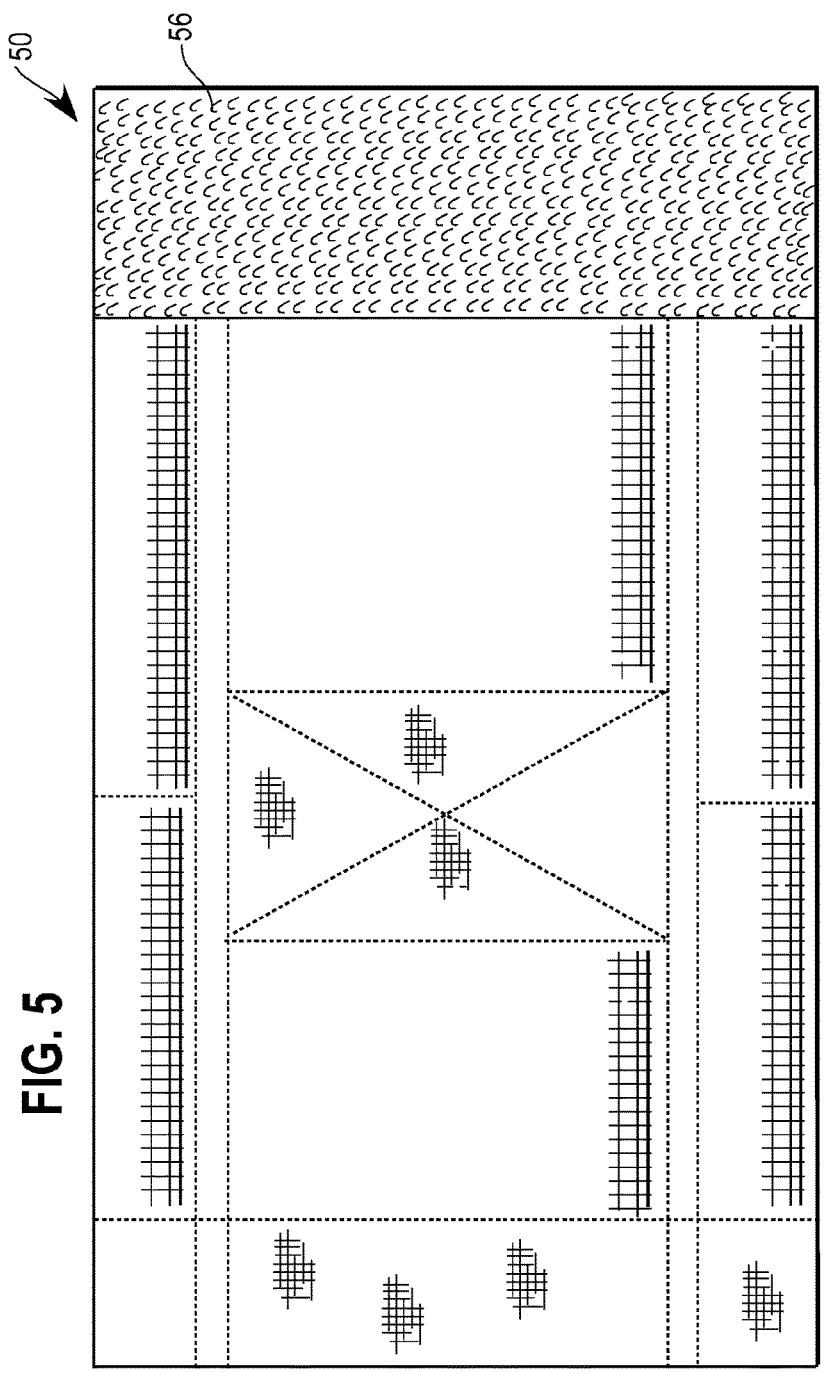
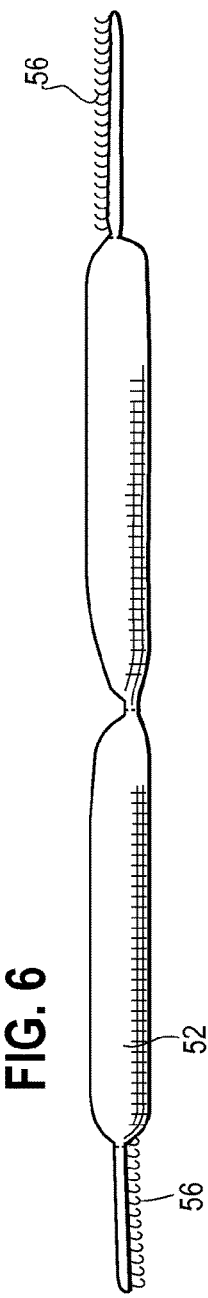
FIG. 5
FIG. 6

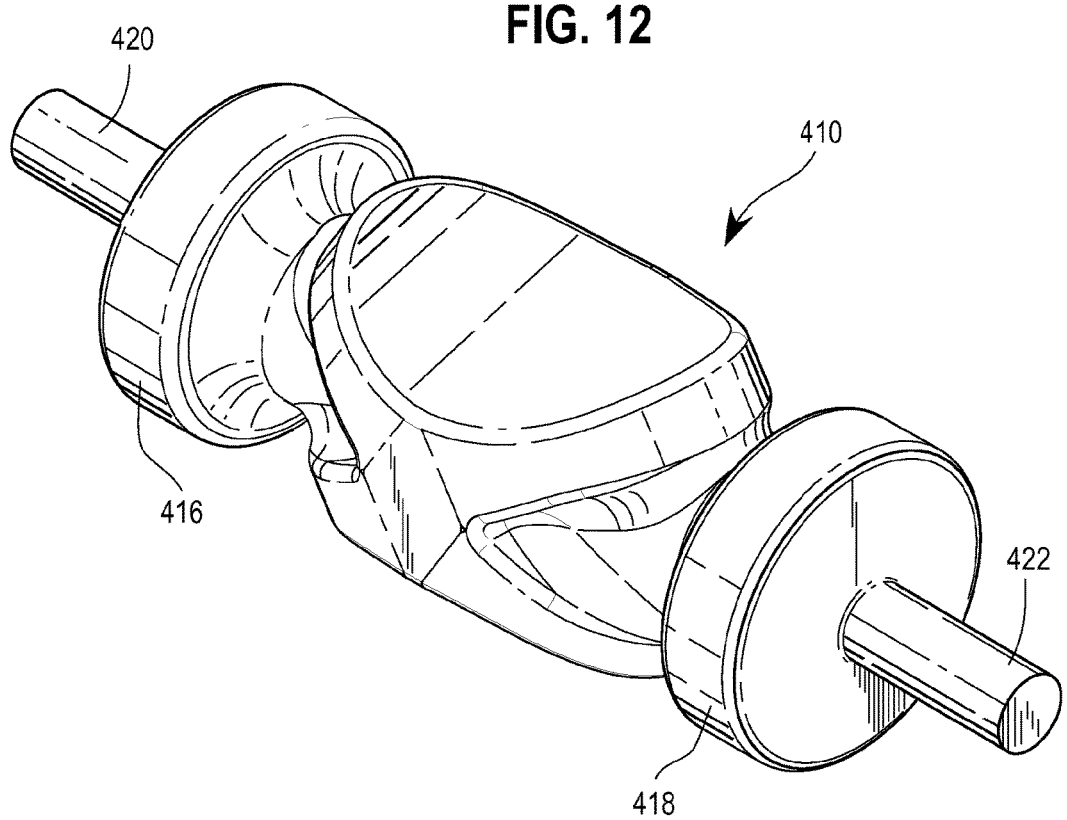

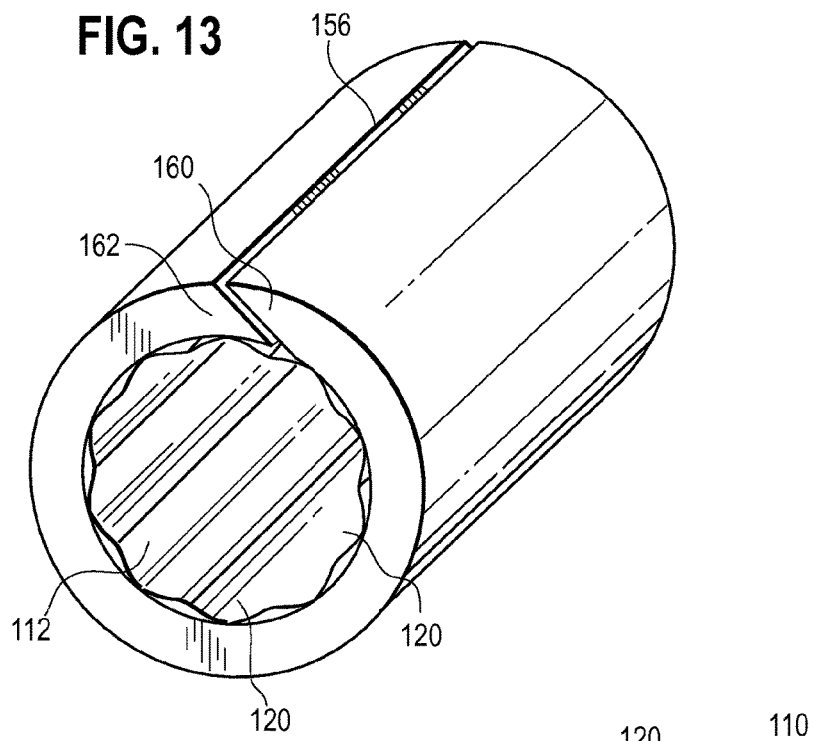
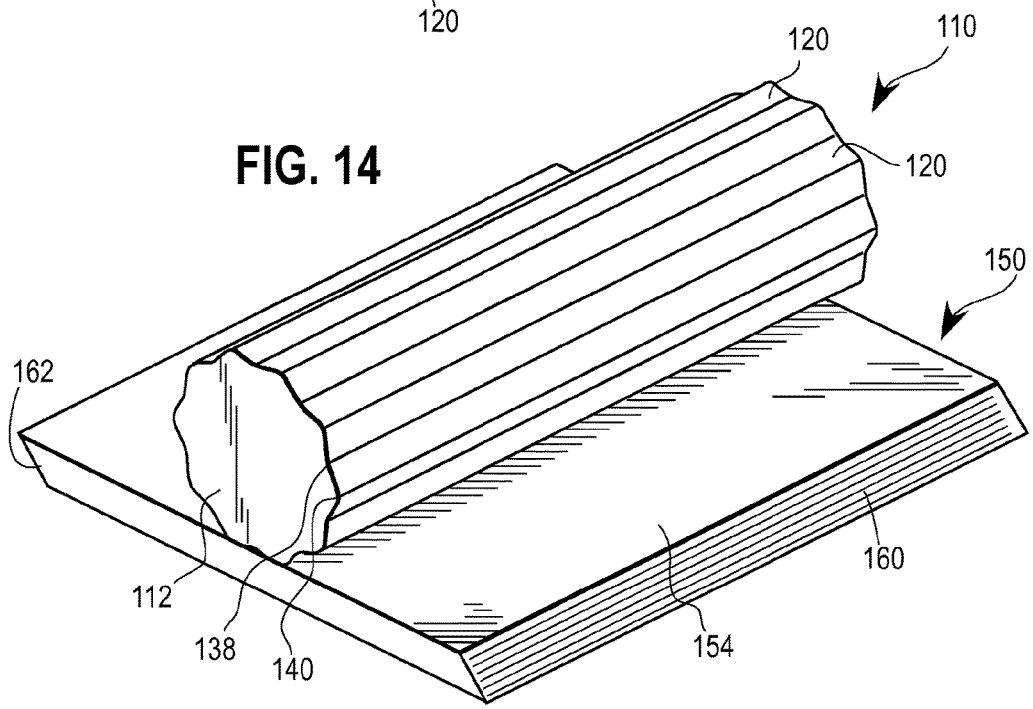

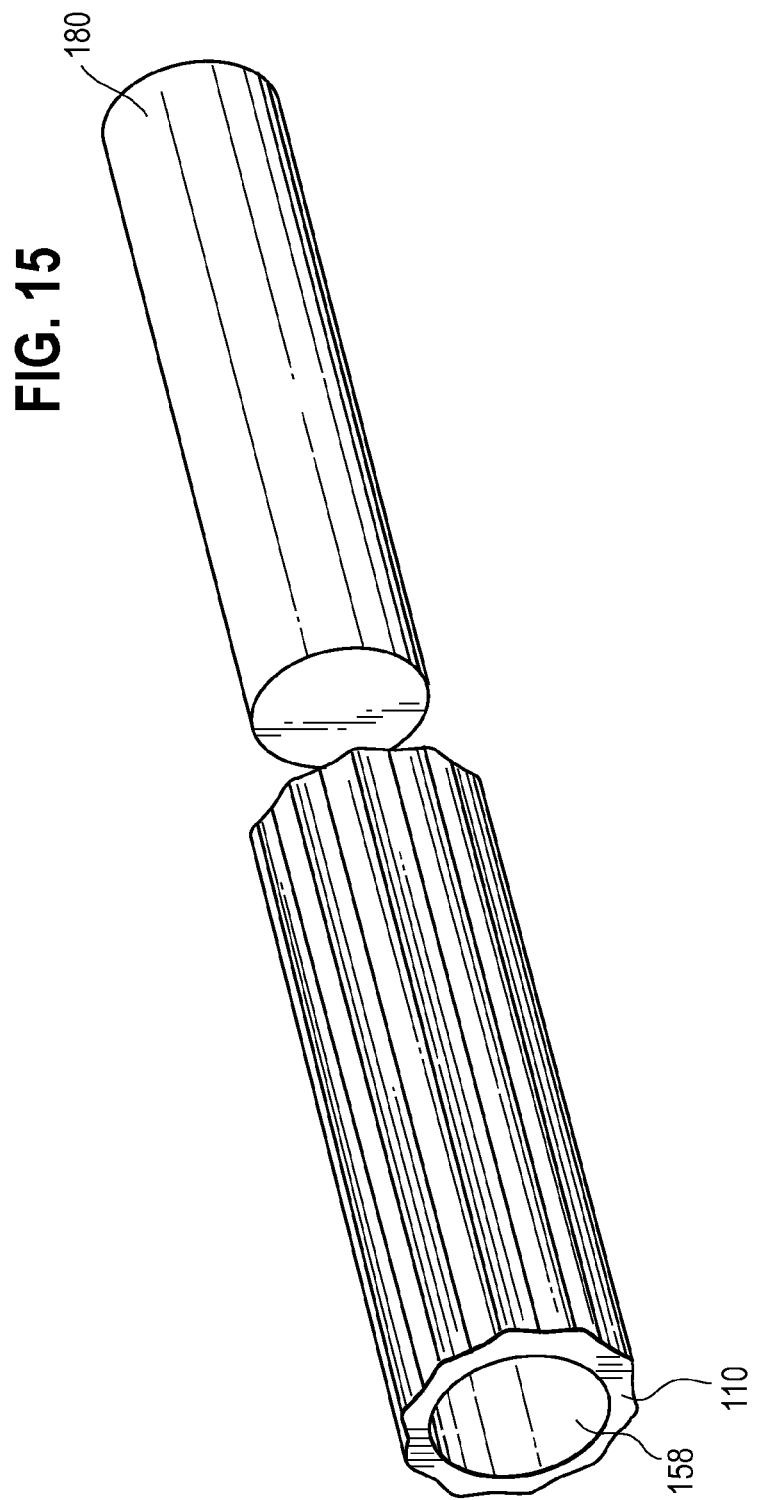

MUSCLE AND TISSUE THERAPY DEVICE

CROSS-REFERENCE TO RELATED PATENT APPLICATIONS

This patent application claims the benefit of U.S. Provisional Patent Application Ser. No. 61/736,589, filed Dec. 13, 2012 and entitled "A Heated Or Cooled Cylinder Used To Stretch Muscles, Relieve Fatigue And Decrease Pain," the disclosures of which are incorporated herein by reference in their entirety.

FIELD OF THE INVENTION

This invention relates generally to the field of massage therapy devices for treating muscle fatigue, soreness, and damage. More particularly, embodiments of the present invention relate to devices that provide therapeutic thermal and pressure therapy to the body.

BACKGROUND OF THE INVENTION

Massage therapy and other types of physical therapy are commonly used to treat fatigued, injured, and sore portions of the body. Such therapy is commonplace for individuals who have discomfort arising from exercise or strenuous activity. This therapy is also useful to provide treatment to muscles, tendons, joints, bones and other tissues of the body that have been injured or strained.

Various devices and equipment are known in the art that are used to enhance and assist the application of therapy to injured or sore body parts. Many of these devices resemble rollers that are used to knead the various parts of the body. These rolling devices known in the art provide a generally uniform rolling surface that applies consistent pressure and force as the device is rolled. There is a need for a pressure massage device having improved shape and design features to allow specific portions of muscles and tissue to be focused upon and isolated during therapy.

The application of different temperature to the subject tissue through hot therapy and cold therapy is also commonly used. The application of low temperature to tissue promotes several positive results, such as vasoconstriction, anti-inflammation, and pain reduction or partial numbing. The application of high temperature to tissue promotes several positive results such as increased blood flow and circulation, and muscle relaxation. In some circumstances, the application of heat and cold is alternated during a therapy session to provide localized relief at a specific location.

Some of the massage devices known in the art are made from materials that can be heated or cooled prior to being placed into contact with tissue. In most cases, the material being heated or cooled is the roller itself. Heating the roller or material inside the roller can be onerous and difficult. There is a need for a pressure massage device having removable means that can be heated or cooled separately from the massage device, and placed onto the massage device as needed.

Physicians, physical therapists and athletic trainers commonly apply or oversee the application of massage therapy. Many of the therapy devices known in the art are designed for a therapist to apply therapy to a patient or client, rather than for an individual to provide therapy to his or her own body. Therapy devices known in the art typically require a second person to effectively apply therapy to the patient or subject. There is a need for a pressure massage device that allows a user to effectively apply therapy to his or her own body without the assistance of a second person.

Accordingly, it is a general object of the present invention to provide an improved physical therapy device that can be operated effectively by a single individual. Another object of the present invention is to provide a physical therapy device having improved shape and design features to allow specific portions of muscles and tissue to be focused upon and isolated during therapy. A further object of the present invention is to provide a physical therapy device having removable means that can be heated or cooled separate from the massage device itself. A still further object of the present invention is to provide a uniquely configured and aesthetically pleasing physical therapy device.

BRIEF SUMMARY OF THE INVENTION

Embodiments of the present invention relate to a roller device for use with massage and physical therapy of the human body. These embodiments are particularly suited to provide thermal therapy to muscle and other tissue using hot or cold members in conjunction with the roller device. The embodiments of the present invention provide a unique combination of thermal elements and physical massage elements that allow for highly customized tissue therapy to be applied to an individual user. The unique configuration of the present invention increases the versatility of the roller device and allows for therapy application to be easily altered and individually focused.

In one preferred embodiment, a roller includes a base cylinder between a first circular end and a second circular end with a ridge structure located on the base cylinder between the circular ends. The ridge structure can be X-shaped and can be formed from four arms extending from a central area of the base cylinder forming lobes which define massage planes and peaks that are optimal for physical manipulation of muscle and other tissue.

In another embodiment of the massage therapy device, a roller includes a substantially cylindrical base extending along a longitudinal axis between a first end and a second end, and a thermal cover having an attachment mechanism and a cavity containing thermal retention fill. The thermal cover is removably attachable to the roller by wrapping the thermal cover around at least a portion of the cylindrical base. The thermal cover can be made from various materials including heavy gauge canvas or denim. The thermal retention fill is capable of retaining thermal energy by being heated or cooled.

The roller can optionally include a ridge structure located between the first end and second end, and the ridge structure can have a generally X-shaped profile formed from a plurality of arms extending from the cylindrical base. The roller can also include raised wheel-shaped disks extending from the first and second ends of the cylindrical base. These disks preferably have a common axis of rotation with the cylindrical base. These disks optionally can have a thickness of about one quarter the diameter of the disks themselves.

The thermal retention fill of the thermal cover can be formed from such materials as rice, seed, grain, corn, metal beads, plastic beads, gel, oil, water and a combination of these materials. The attachment mechanism of the thermal cover can be formed from such materials as hook and loop fasteners, zippers, snaps, buttons, ties, straps, clasps, cords, magnets, adhesive and a combination of these materials. The roller optionally can be formed from such materials as polyethylene, cross-linked polyethylene, polyurethane, reticulated polyurethane, polypropylene, polystyrene, polyvinyl chloride, nylon, polycarbonate, and a combination of these materials. The roller can be formed from rotationally molded materials such as thermoplastic and other rotationally molded materials known in the art. The roller can also be formed from machined materials such as wood, metal, and other machined materials known in the art.

In another embodiment of the invention, a cylindrical roller includes an elongate core member having a longitudinal axis and a diameter and terminating in end portions of a relatively larger diameter, and a plurality of lobes on the core member extending outwardly from the core member at an acute angle relative to the longitudinal axis of the core member and defining ribbon-like external contact surfaces around the periphery of the lobes. A first lobe optionally can intersect with a second lobe to form an intersection angle between about 150 degrees and about 70 degrees. The elongate core member and the plurality of lobes may be formed as a single unitary piece. The cylindrical roller may be tubular with a hollow interior cavity, or solid without a hollow interior.

The cylindrical roller can also include a thermal cover detachably connected to the roller, with the thermal cover having an attachment mechanism or fastener and a cavity containing thermal retention fill (such as corn).

In another embodiment of the massage therapy device, a roller includes an elongate core member having a longitudinal axis and a diameter and terminating at each end in wheel-shaped disks of a relatively larger diameter relative to the elongate core. At least one pair of opposed lobate structures extend outwardly from the core member and define ribbon-like external contact surfaces around the periphery of each lobate structure, and the first lobate structure intersects with the second lobate structure to form an intersection angle of about 140 degrees. A thermal cover having a hook and loop fastener and a sealed cavity containing corn is removably attachable to the roller by wrapping the thermal cover around at least a portion of the cylindrical base and securing the hook and loop fastener. The thermal retention fill is capable of being heated or cooled and retaining this thermal energy. Optionally, the roller has a length of about fifteen inches and the wheel-shaped disks have a diameter of about six inches. Each lobate structure may optionally form a semi-circular flat face having a length of about six inches at its longest dimension. Each wheel-shaped disk may have the same diameter as the other disk. Optionally, the external surfaces of at least one lobate structure extend above the surface of the elongate member to form a raised peak.

In another embodiment of the present invention, a roller includes a base cylinder with a series of ridges that extend along the length of the roller. The ridges are regularly spaced around the roller, and form peaks and valleys that can be used as pressure points to apply alternating pressure to muscles and other tissue. In another embodiment of the invention, a roller includes a hollow cavity that accepts a thermal retention plug.

A thermal cover can be used in conjunction with the various embodiments of rollers of the present invention. In one embodiment, a cover constructed of fabric material includes an interior cavity containing a thermal retention fill that can be heated or cooled. The cavity may be permanently closed, or may be accessible through an access passage that can be unsealed and resealed. The cover includes a fastening mechanism that allows the cover to be removably attached to the roller.

Various features of the inventive roller and cover are discussed and disclosed in the following description. Other features, objects, advantages, aims, embodiments, applications and the like will be apparent to those skilled in the art from the present description taken with the accompanying drawings and appended claims.

BRIEF DESCRIPTION OF THE DRAWINGS

FIG. 5 is a top view of the thermal cover of FIG. 4.

FIG. 6 is a side view of the thermal cover of FIG. 4

FIG. 12 is a perspective view of an alternative embodiment of a massage roller of the present invention.

FIG. 13 is a perspective view of an alternative embodiment of a thermal cover attached to a massage roller of the present invention.

FIG. 14 is a perspective view of the thermal cover of FIG. 13 partially engaged with the massage roller of FIG. 13.

FIG. 15 is a perspective view of an alternative embodiment the massage roller of the present invention.

DETAILED DESCRIPTION OF THE INVENTION

Figure 1:
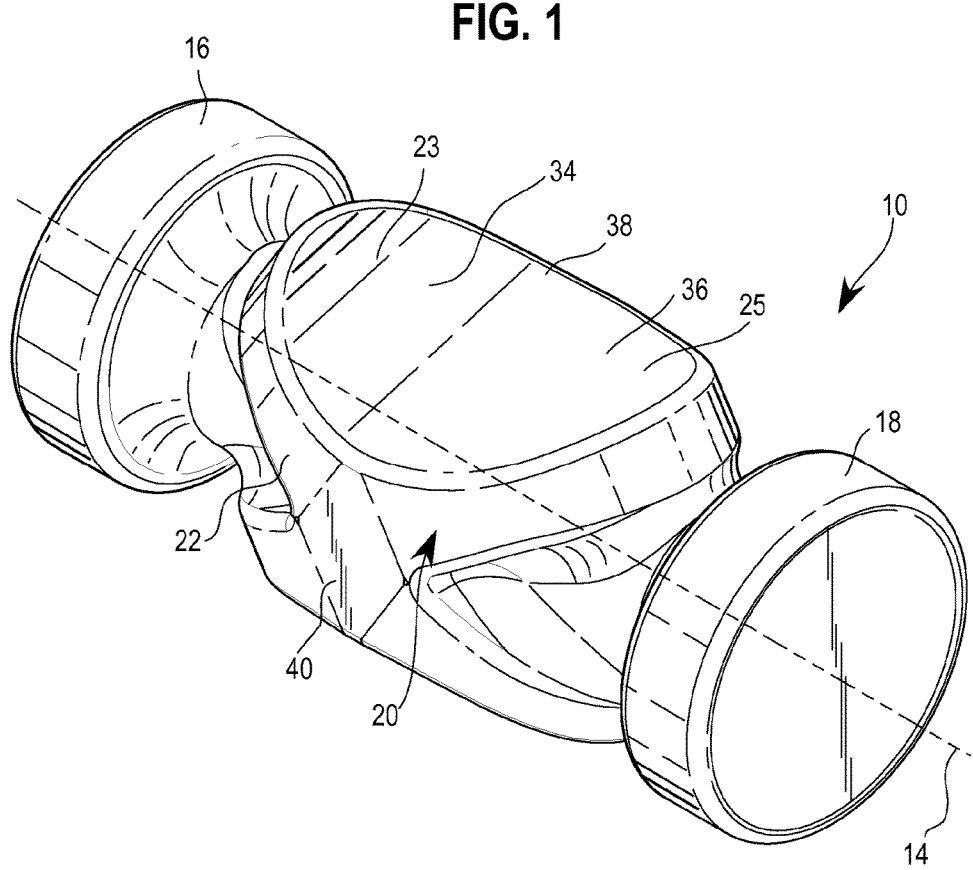
FIG. 1 is a perspective view of one embodiment of a massage roller of the present invention.

The invention or inventions disclosed herein are susceptible to embodiments in many different forms. The embodiments shown in the drawings and described in detail below are provided for illustrative purposes. The disclosure is intended as an exemplification of principles and features of the invention as illustrated by the embodiments described herein.

Figure 2:
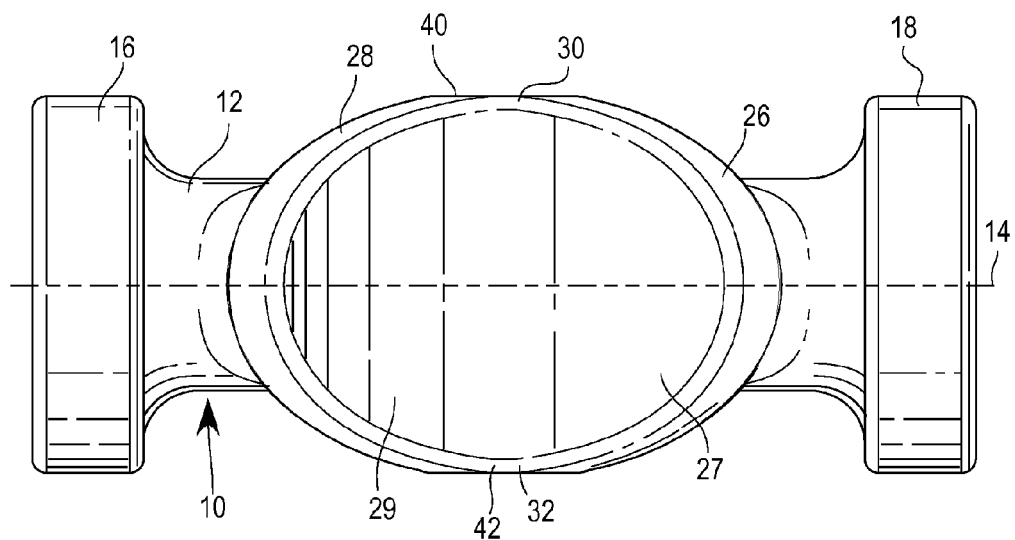
FIG. 2 is a side view of the massage roller of FIG. 1.
Figure 3:
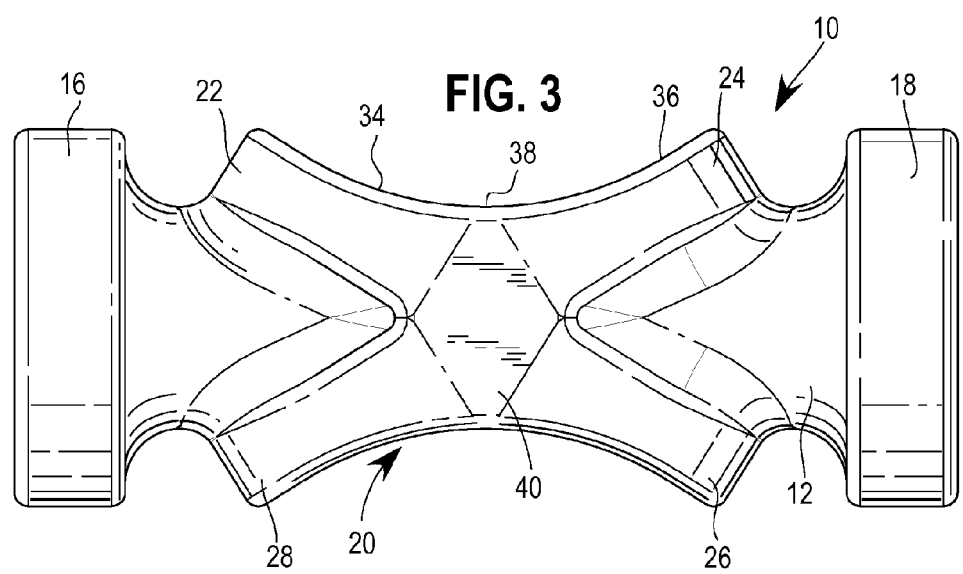
FIG. 3 is a top view of the massage roller of FIG. 1.
Figure 4:
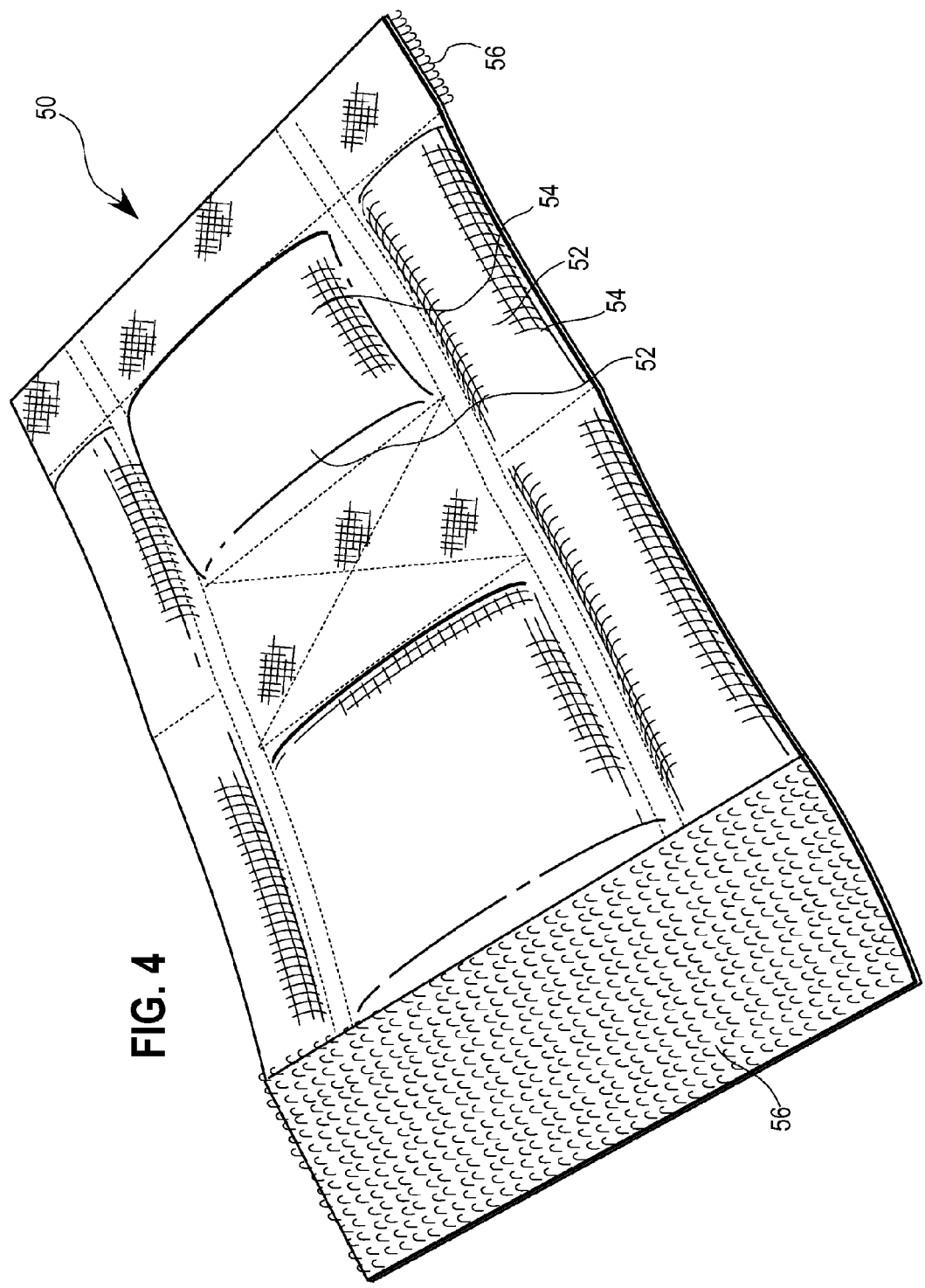
FIG. 4 is a perspective view of one embodiment of a thermal cover of the present invention.
Figure 7:
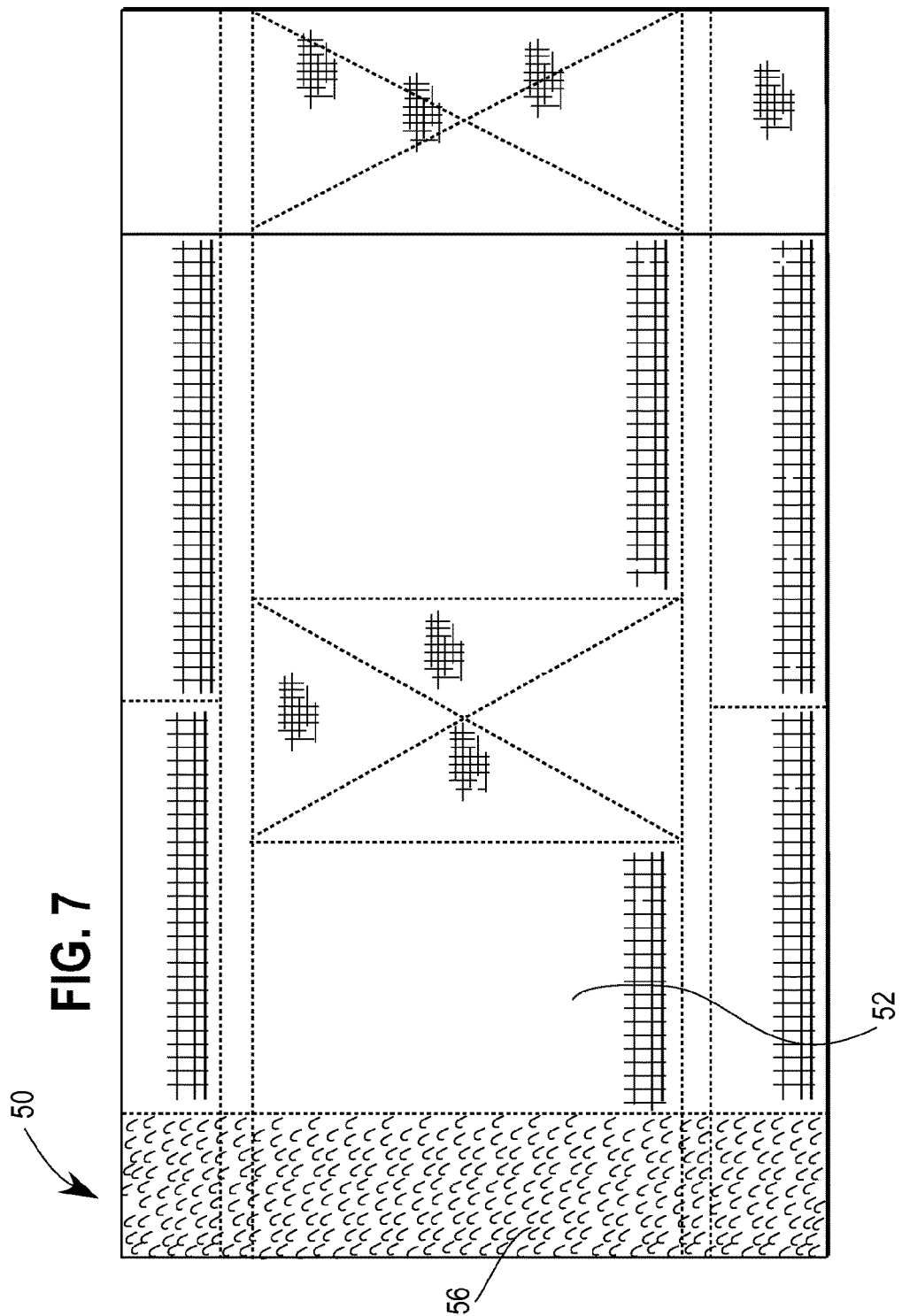
FIG. 7 is a bottom view of the thermal cover of FIG. 4.

Referring to the drawings, FIGS. 1-3 show an embodiment of a roller 10 in accordance with one aspect of the invention. Preferably, roller 10 is constructed of foam-type materials such as polyethylene foam, cross-linked polyethylene foam, polyurethane foam, reticulated polyurethane foams, polypropylene, polystyrene, polyvinyl chloride, nylon, and polycarbonate. Preferably, roller 10 is formed from a closed-cell foam material.

The use of foamed materials provides the advantage of reducing the total mass of the roller, while maintaining strength to allow the roller to retain its shape when force is exerted against it. The reduction in mass results in roller 10 being easier to transport and handle. The use of foamed material provides the additional advantage of reducing the heat capacity and thermal conductivity of the roller 10, which reduces the amount of thermal energy that the roller 10 absorbs when in contact with a thermal source such as thermal cover. This reduction of thermal absorption by roller 10 in turn increases the amount of thermal energy that is transferred from a thermal source to a treatment area on a user's body.

Alternatively, roller 10 can comprise other materials know in the art, including but not limited to plastics, wood, metal, and composite materials. Roller 10 can also comprise rotationally molded materials such as thermoplastics.

Roller 10 includes base cylinder 12 that extends along a longitudinal axis 14 between a first end 16 and a second end 18. Ends 16, 18 preferably are circular and have diameters greater than the diameter of base cylinder 12 such that ends 16, 18 extend beyond and encircle the base cylinder. Ends 16, 18 may also have various other shapes, such as frusto-conical. In one embodiment, ends 16, 18 are located on the terminal ends of base cylinder 12. Alternatively, ends 16, 18 can be located on an intermediate portion of base cylinder 12 such that a portion of base cylinder 12 extends beyond ends 16, 18. FIG. 12 illustrates an embodiment of a roller 410 having handles 420, 422 extending beyond ends 416, 418. Handles 420, 422 provide additional gripping surfaces to allow a user to manipulate the roller.

Roller 10 further includes a ridge structure 20 located on the base cylinder 12 between ends 16, 18. Preferably, ridge structure 20 is an X-shaped ridge formed from four arms extending from a central area of base cylinder 12. With reference now to the top view of roller 10 of FIG. 3, arms 22, 24, 26, and 28 are shown extending from base cylinder 12 to form a generally X-shaped ridge structure 20 when viewed from this angle. The arms extending from the base cylinder form lobes that extend from one side of the base cylinder to an opposite side of the base cylinder. For example, arm 22 forms lobe 23, which is preferably a semi-circle structure as shown in FIG. 2. Arms 22, 24, 26, and 28 form lobes 23, 25, 27 and 29, respectively.

Preferably, arms 22, 24, 26 and 28 generally each have the same length, as shown for example in the embodiment of FIGS. 1-3. Alternatively, arms 22, 24, 26 and 28 may vary in length such that one arm may be longer than the other arms, or a pair of arms may be longer than the other pair of arms. Arms being equal in length may be beneficial to certain types of muscle therapy when the roller 10 is utilized, whereas arms being unequal in length may be beneficial for different types of muscle therapy.

Likewise, arms 22, 24, 26 and 28 preferably each form the same angle relative to longitudinal axis 14. Alternatively, arms 22, 24, 26 and 28 may form different angles relative to longitudinal axis 14 such that an asymmetrical ridge structure is formed. Arms having the same angles and forming a symmetrical X-shape ridge may be beneficial for some types of therapy, whereas arms forming an asymmetrical shape may be advantageous for other therapy situations.

As shown in the side view of FIG. 2, lobes 23, 25, 27 and 29 define massage planes that extend from a top surface 30 to a bottom surface 32 of roller 10. For example, lobe 23 defines massage plane 34, and lobe 25 defines massage plane 36. Similar massage planes are defined by lobes 27 and 29 on the roller opposite lobes 23 and 25. In the embodiment of the roller shown in FIGS. 1-3, lobes 23 and 25 are paired together in a team to form adjacent massage planes 34 and 36 that intersect to create valley 38. This valley 38 formed by the teaming of lobes 23 and 25 is beneficial to some types of therapy, as discussed further below. Preferably, the intersection of adjacent planes (such as planes 34 and 36) creates a generally U-shaped valley as shown, for example, in FIG. 3. Alternatively, the intersection between adjacent massage planes is more pronounced and creates a generally V-shaped valley. The angle of the valley 38 formed by the intersection of adjacent massage planes can vary between about 170 degrees and about 10 degrees, and preferably the angle is between about 150 and about 130 degrees.

Also in the embodiment of the roller shown in FIGS. 1-3, lobes 23, 25, 27 and 29 intersect to create first peak 40 and second peak 42. With reference to FIG. 2, peaks 40 and 42 preferably extend beyond the surface of base cylinder 12 to create a raised peak. Preferably peaks 40 and 42 extend from the base cylinder 12 the same distance as the first and second ends 16, 18 extend from the base cylinder 12 such that peaks 40 and 42 are generally level with ends 16, 18. Preferably the ends have a diameter of about 6 inches and the peaks are spaced apart a distance of 6 inches in this configuration. A roller 10 having such a configuration allows peak 40 and ends 16 and 18 to contact a generally flat surface simultaneously. In this manner, the roller 10 can be placed on a generally flat portion of an individual's body (such as a back or thigh) and the roller 10 contacts this body surface at three separate points simultaneously.

Alternatively, peaks 40 and 42 can extend to a distance greater than the distance than first and second ends 16, 18 extend from the base cylinder 12 such that peaks 40 and 42 are generally higher than ends 16, 18 in relation to longitudinal axis 14. A roller 10 having such a configuration allows peaks 40 and 42 to contact a generally flat surface without ends 16 and 18 contacting that surface simultaneously. In this manner, the roller 10 can be placed on a generally flat portion of an individual's body (such as a back or thigh) and the roller 10 contacts this body surface only at the single peak point coinciding with peak 40 or 42.

Alternatively, peaks 40 and 42 can extend to a distance less than the distance that first and second ends 16, 18 extend from the base cylinder 12 such that peaks 40 and 42 are generally lower than ends 16, 18 in relation to longitudinal axis 14. Likewise, peaks 40 and 42 can be flush with the surface of base cylinder 12. A roller 10 having such a configuration allows ends 16 and 18 to contact a generally flat surface without peaks 40 and 42 contacting that surface simultaneously. In this manner, the roller 10 can be placed on a generally flat portion of an individual's body and the roller 10 contacts this body surface only at the two points coinciding with ends 16, 18.

Roller 10 can be sized in a variety of dimensions for use in a variety of therapy applications. The length along longitudinal axis 14 and the diameter of first and second ends 16,18 can be dimensioned for use in full-body therapy or for therapy of larger body parts such as the back and shoulders. In a particularly preferred embodiment of the roller 10, the roller has a length of about 15 inches and a diameter of about 3.5 inches. The diameter of the first and second ends is about 6 inches, and the thickness of each end is about 1.75 inches. Roller 10 can also be dimensioned to apply therapy to smaller body parts such as arms and legs. In another embodiment designed for such use, the roller ranges in length from about 6 to 8 inches and the diameter of the first and second ends range in size from about 2 to 4 inches.

Referring to the drawings, FIGS. 4-7 show an embodiment of a thermal cover 50 in accordance with one aspect of the invention. Preferably, cover 50 is constructed of fabric material, and more preferably heavy gauge canvas or denim. Alternatively, cover 50 can be constructed from many materials known in the art, including but not limited to textiles, woven materials, non-woven materials, and rubber materials.

Cover 50 preferably includes an interior cavity 52 that envelopes a thermal retention fill 54. Thermal retention fill 54 can be permanently or semi-permanently enclosed within the cover 52. Alternatively, interior cavity 52 may be fully or partially accessible through an access passage that can be temporarily closed with snaps, hook and loop fasteners, zippers and the like. Preferably, thermal retention fill 54 comprises natural materials capable of retaining heat or cold such as rice, seed or grain, and more preferably corn. Alternatively, thermal retention fill 54 can comprise other materials know in the art, including but not limited to metal beads, plastic beads, gels, oils, water, chemical compositions and other aqueous solutions.

Cover 50 can also be a unitary material that acts as a thermal retention material itself without the need for a cavity containing separate thermal fill. Covers of this type preferably comprise rubber, plastic, polymers and other materials capable of holding thermal energy when heated or cooled.

Cover 50 is dimensioned to be removably attached to roller 10. Preferably cover 50 is dimensioned to be inserted between ends 16 and 18 in a manner that allows cover 50 to wrap around roller 10 such that base cylinder 12 and ridge structure 20 are completely encircled by cover 50 while ends 16, 18 remain uncovered. Alternatively, cover 50 can be dimensioned to cover the entire length of roller 10, including ends 16 and 18 such that cover 50 wraps around the entire roller 10. In a preferred embodiment for use with a collar having a length of 15 inches, for example, cover 50 can have a width of about 12 inches and a length of about 22 inches.

Cover 50 includes attachment mechanism 56 that allows cover 50 to be securely fastened to roller 10. Preferably, attachment mechanism 56 includes a hook and loop fastener such as VELCRO brand fasteners or other similar material. Alternatively, attachment mechanism 56 can comprise other mechanisms known in the art, including but not limited to zippers, snaps, buttons, ties, straps, clasps, magnets, adhesive and cords. Preferably, cover 50, fill 54 and attachment mechanism 56 are comprised from material that is compatible with use in a microwave oven.

Figure 8:
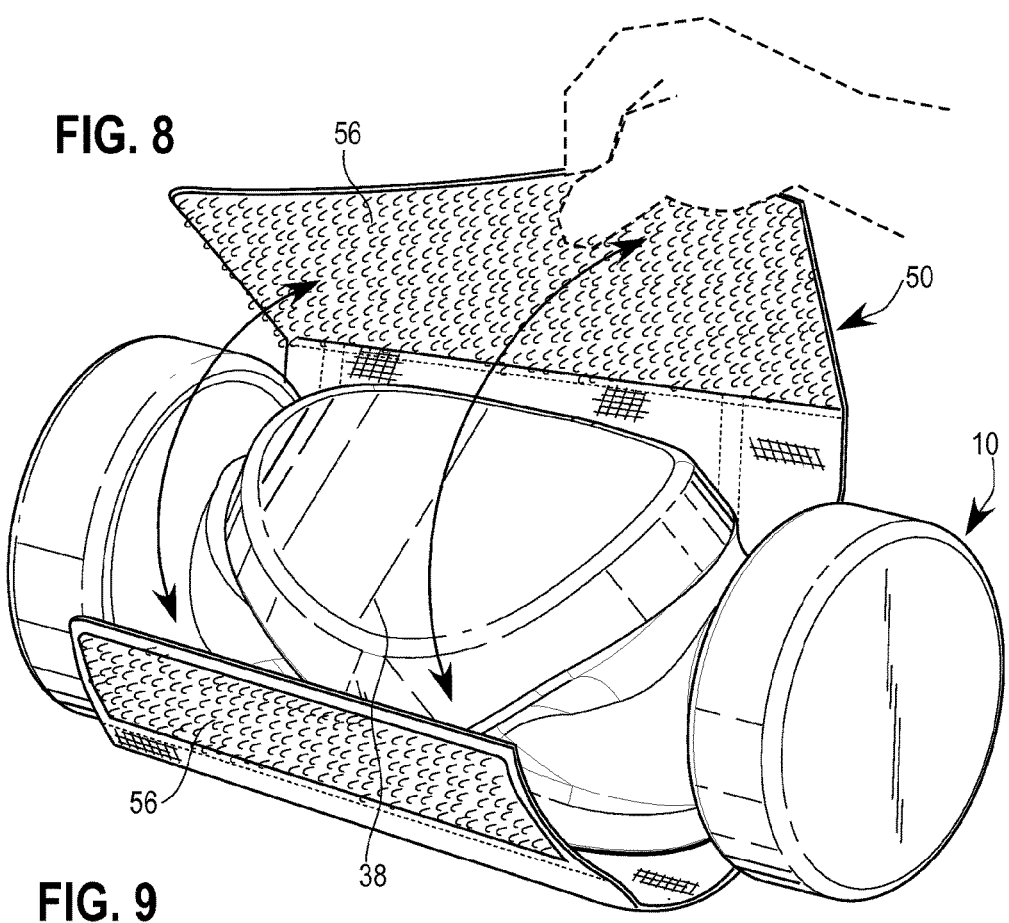
FIG. 8 is a perspective view of the thermal cover of FIG. 4 partially engaging the massage roller of FIG. 1.
Figure 9:
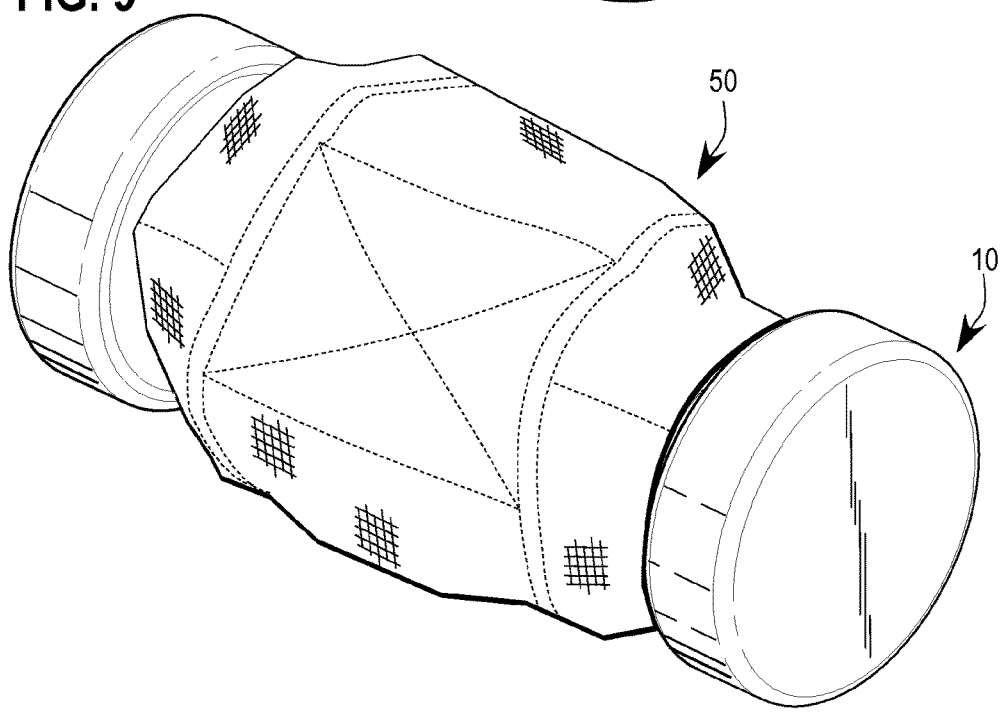
FIG. 9 is a perspective view of the thermal cover of FIG. 4 attached to the massage roller of FIG. 1.

In one embodiment of the invention, as shown in FIGS. 8 and 9, cover 50 can be attached to roller 10 by positioning cover 50 into a flattened position and then placing the roller onto the flattened cover. Cover 50 is then wrapped around roller 10 and opposite ends of cover 50 are attached with attachment mechanism 56. When cover 50 is wrapped around roller 10, preferably thermal retention fill 54 is conformed to the cavities on roller 10 created at valley 38 and other portions of the roller. Preferably, the resulting shape when cover 50 is wrapped around roller 10 is a generally cylindrical shape lacking sharp corners that can easily roll. To remove cover 50 from roller 10, the attachment mechanism 56 is decoupled and cover 50 is unwrapped from roller 10.

Figure 10:
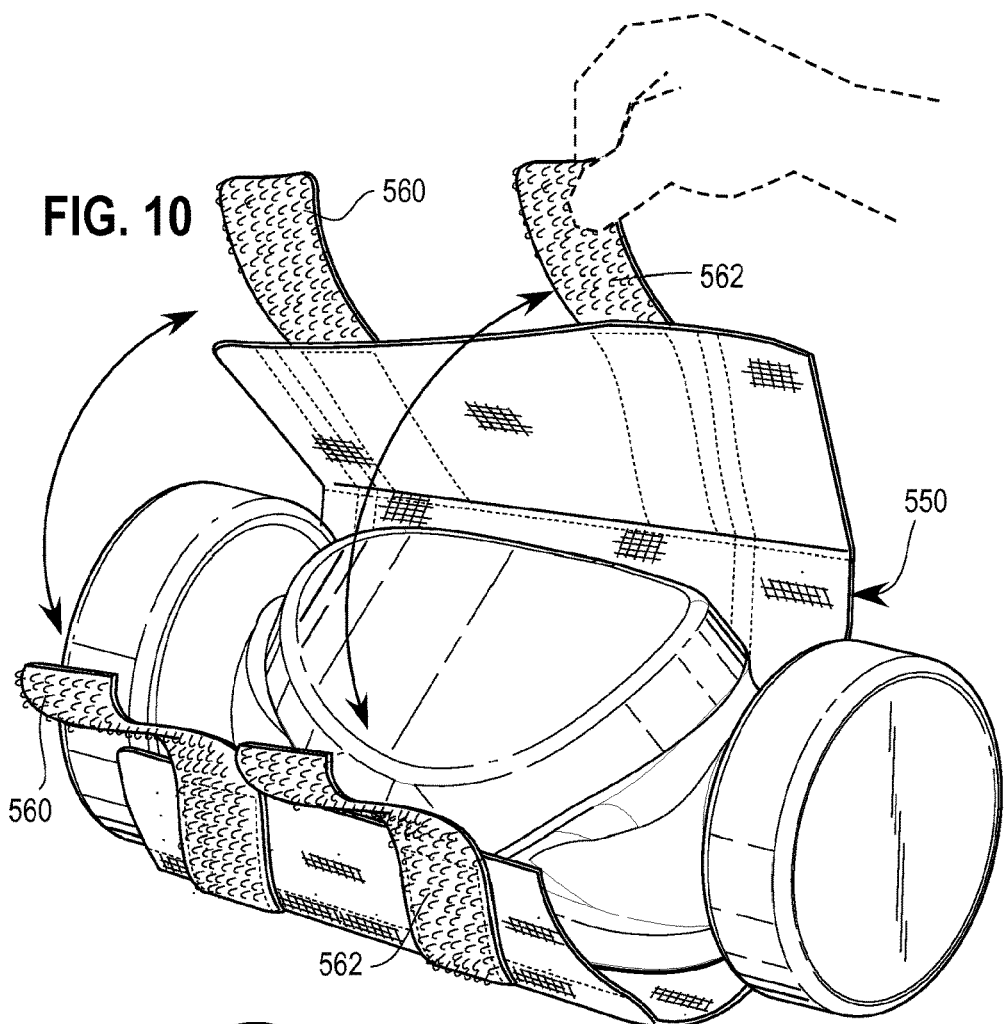
FIG. 10 is a perspective view of an alternative embodiment of a thermal cover of the present invention partially engaging the massage roller of FIG. 1.
Figure 11:
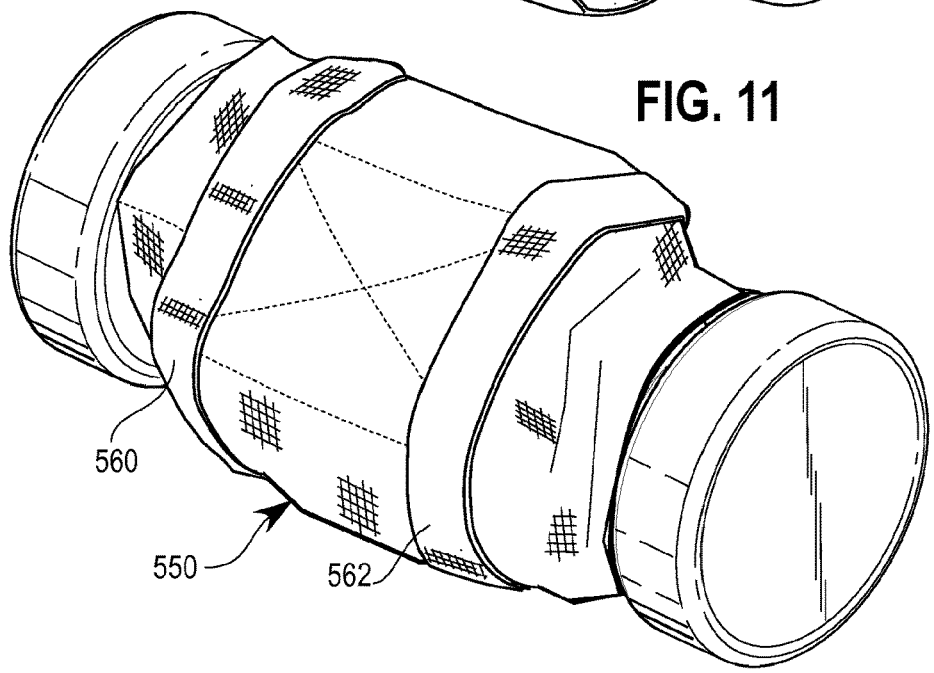
FIG. 11 is a perspective view of the thermal cover of FIG. 10 attached to the massage roller of FIG. 1.

FIGS. 10 and 11 illustrate an alternative embodiment of the cover 550 having straps 560, 562 that are used to secure cover 550 to the roller. Straps 560, 562 have two ends that preferably are attached to each other when the cover 550 is attached to roller. The two ends of the straps can be connected by various means including snapping, buttoning, or use of hook and loop fasteners. The ends of the straps can also be tied to each other.

The thermal retention fill 54 of cover 50 can be heated or cooled in a variety of manners so that the fill can retain thermal energy for later application to an individual during therapy. Preferably, cover 50 is heated or cooled when it is detached from roller 10.

Cover 50 can be placed into a freezer or refrigerator in order to cool fill 54. The cooled temperature of fill 54 can be varied by varying the amount of time cover 50 is placed into a freezer. In a preferred embodiment in which fill 54 is comprised of corn or similar material, placing cover 50 into a freezer for at least five hours provides a maximum cooled temperature for fill. A user can place cover 50 into a freezer for various shorter times to obtain the desired cooled temperature for fill 54.

Likewise, cover 50 can be placed in a microwave oven in order to heat fill 54. The heated temperature of fill 54 can be varied by varying the amount of time cover 50 is heated in the microwave oven. Preferably, cover 50 is heated in a microwave oven for up to two minutes to reach a desired heated temperature of fill 54. Alternatively, cover 50 can be heated in a conventional oven, in boiling water, in a clothes dryer, or by other methods of heating known in the art.

In another embodiment, induction heating can be used to heat cover 50 by applying an electric current to the heat fill 54. In such an embodiment, fill 54 preferably comprises metal beads or other material with relatively low electrical resistance. Alternatively, exothermic chemical reactions (such as crystallization or oxidation) can be used to heat fill 54. Likewise, endothermic reactions can be used to cool fill 54. Heating or cooling the fill 54 by such chemical reactions provides the additional benefit of providing ongoing thermal output as the chemical reaction occurs, which in turn prolongs the thermal effect on the cover 50 for a correspondingly longer time.

The thermal cover 50 allows for the application of beneficial thermal therapy to targeted tissue areas. Application of low temperature to tissue promotes several positive results, such as vasoconstriction, anti-inflammation, and pain reduction or partial numbing. The application of low temperature also can help reduce pain and swelling of muscle and other tissue. The application of high temperature to tissue promotes increased blood flow and circulation, and muscle relaxation. In some circumstances, the application of high and low temperature is alternated during a therapy session to provide the benefit of both heat and cold therapy.

The removability of cover 50 from roller 10 creates a versatility that provides several benefits and advantages for a user. For example, roller 10 can be used by itself for therapy without cover 50 being attached. Such bare roller therapy may be highly desirable in therapy situations in which heightened physical manipulation of muscle and tissue using the ridge structure 20 is desired. If temperature therapy is not necessary, a room temperature cover 50 can be attached to roller 10 to reduce the pressure points provided by the ridge structure 20. The ability to attach and remove the cover 50 from roller 10 allows a user to vary the pressure point profile of the therapy roller device as necessary for various therapies.

The removability of cover 50 also allows a user to easily and conveniently apply temperature therapy without the need to heat or cool roller 10 itself. Cover 50 can be folded and manipulated into freezer space or microwave space much more readily than the bulky and rigid roller 10. In some cases, roller 10 will not fit into a microwave or small freezer at all, so more burdensome methods of heating or cooling would be necessary. Removability of cover 50 increases the versatility and usability of the roller device by allowing a user to have multiple covers for ready use. For example, a user can store one cover in a freezer while he or she uses the roller alone or with a second cover that has been heated or cooled to a desired temperature. The ability to use multiple covers allows a user to apply cold therapy for a prolonged period of time by using multiple cold temperature covers consecutively without a delay to re-cool the single roller or single cover. It also allows for improved use of temperature therapy rotation between hold and cold temperature application, because multiple covers can be rotated through the therapy session without requiring a single cover to be heated and cooled during the same therapy session. For these and other reasons, the removability of cover 50 greatly increases the versatility and usability of this embodiment of the present invention.

In use, the unique configuration of the ridge structure allows highly beneficial physical therapy to be applied to muscles and other tissue. For therapy applications that require the application of pinpoint pressure to a specific body location, peaks 40, 42 can be used to apply focused pinpoint pressure. For therapy applications that require pressure to be applied around an area of no pressure application, the valley 38 of roller 10 can be positioned above the area of no pressure and the surrounding lobes 23, 25 will apply pressure to adjoining tissue areas. For therapy applications that require the application of constant rolling pressure, ends 16, 18 can be rolled along tissue to provide consistent rolling pressure.

Roller 10 is preferably comprised of rigid material having the strength to withstand a user's body weight. In a preferred embodiment, roller 10 maintains its shape and structure when partial body weight loads are applied to the entire roller and to specific portions of roller 10 such as ridge structure 20 and lobes 23, 25, 27 and 29. Roller 10 having this feature allows a user to rely upon his or her own body weight to assist in applying therapy to muscles and other tissue. For example, roller 10 (with or without cover 50 attached) can be placed upon a hard surface such as a floor and the user can sit, stand or lay upon roller 10 in a manner that applies pressure to the desired portions of user's body.

Reliance upon body weight allows a user to apply therapy to body parts without the need to rely upon the assistance from a second individual, such as a therapist or trainer. The amount of pressure applied to a body part can be adjusted by increasing or decreasing the amount of body weight placed upon the roller. In another embodiment, roller 10 can contain pressure sensors to provide information about the amount of pressure being applied to the roller. This pressure information can be used, for example, to determine the amount of pressure being applied to a particular body part in contact with the roller.

Referring to FIGS. 13-18, additional embodiments of the invention are depicted. FIGS. 13-15 show an embodiment wherein roller 110 has a base cylinder 112 with a series of ridges 120 that extend length-wise along longitudinal axis 114. Preferably, ridges 120 are regularly spaced around the circumference of roller 110. Ridges 120 create peaks 140 and valleys 138 between successive peaks. Peaks 140 preferably form slightly rounded edges. The peaks can be used as pressure points to apply alternating pressure to muscles and other tissue when roller 110 is rolled along a portion of a user's body.

Figure 16:
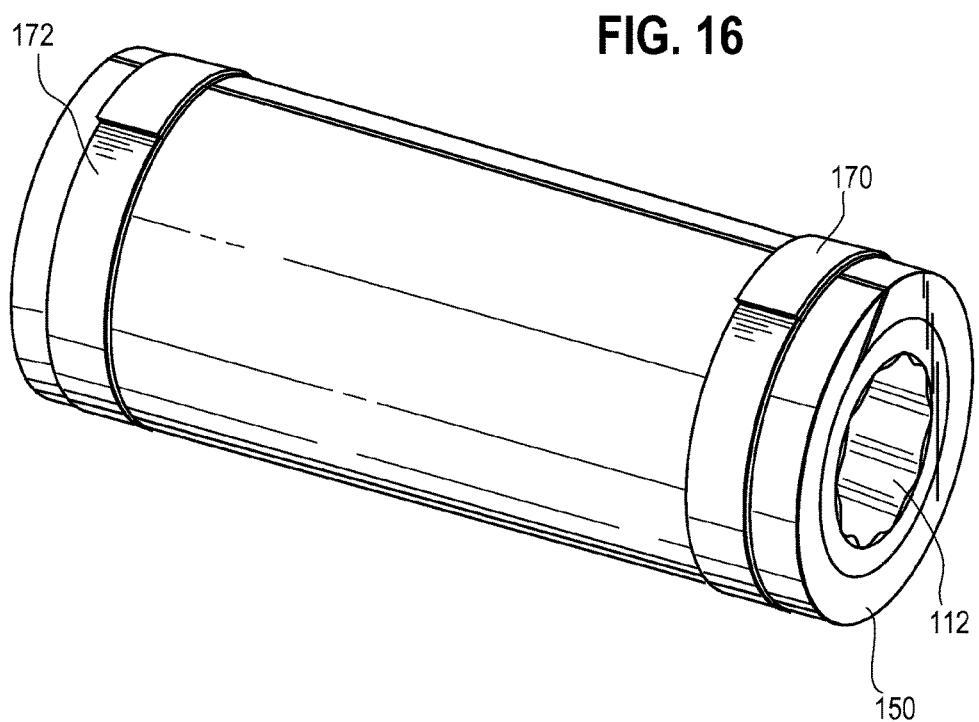
FIG. 16 is a perspective view of an alternative embodiment of a thermal cover attached to a massage roller of the present invention.

Thermal cover 150 can be removably attached to roller 110. Cover 150 contains thermal retention material 154 that can be cooled or heated. Cover 150 preferably is dimensioned to envelope the entire length of roller 110 and to slightly overlap with portions of itself when the cover is wrapped around the circumference of roller 110. As shown in FIGS. 13-14 and 16, cover 150 includes beveled edges 160, 162 that are complementary to one another. Beveled edges 160,162 interface with one another when cover 150 is wrapped around roller 110. Preferably, cover 150 includes an attachment mechanism 156 located near beveled edges 160,162 that allows the two complementary edges to be removably connected to one another.

In an embodiment shown in FIG. 16, cover 150 includes attachment bands 170, 172. Attachment bands 170, 172 encircle cover 150 when the cover is wrapped around roller 110. Attachment bands 170, 172 can be attached to themselves to assist in keeping the cover 150 engaged with roller 110. Attachment bands can contain closure mechanisms known in the art such as snaps, buttons, ties, or hook and loop fasteners such as VELCRO brand fasteners or other similar material.

In an embodiment of the invention shown in FIG. 15, roller 110 includes a hollow cavity 158 that accepts thermal retention plug 180. Thermal retention plug is dimensioned to fit snuggly into hollow cavity 158. Preferably, thermal retention plug 180 contains thermal retention material 154 that retains heat or cold. Alternatively, thermal retention plug 180 itself is constructed from materials that retain heat and cold. In use, the thermal energy contained within the plug is transferred to the roller 110 when plug 180 is inserted into hollow cavity 158. This thermal energy transfer occurs when the outer walls of thermal retention plug 180 are placed into contact with the walls of hollow cavity 158.

Figure 18:
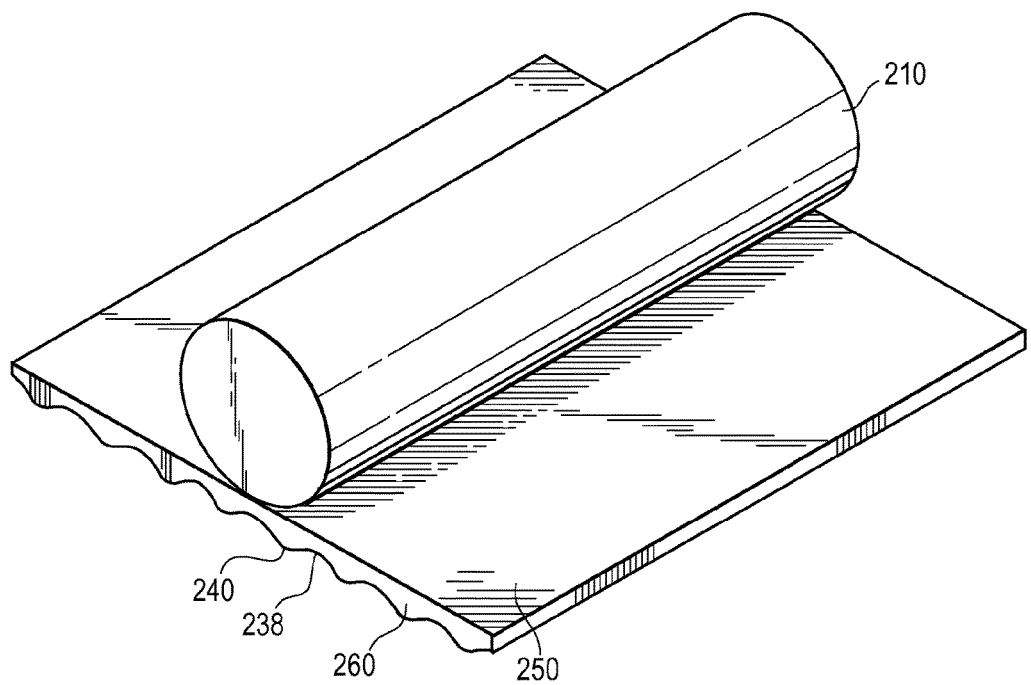
FIG. 18 is a perspective view of an alternative embodiment of a thermal cover partially engaged with a massage roller of the present invention.

In an embodiment of the invention shown in FIG. 18, roller 210 is generally cylindrical and made from rigid material such as plastic, metal, or wood. Preferably, roller 210 is constructed from thermoplastic. Preferably roller 210 comprises a solid cylinder. Alternatively, roller 210 may contain a hollow cavity extending along its longitudinal axis similar to hollow cavity 158 of the embodiment in FIG. 15.

As further shown in FIG. 18, cover 250 includes a series of ridges 260 on one side and a flat surface on the side opposite ridges 260. Preferably, ridges 260 are regularly spaced along one side of cover 250. Ridges 260 create peaks 240 and valleys 238 between successive peaks. Peaks 240 preferably form slightly rounded edges. Cover 250 can be removably attached to roller 210 in the manner described herein regarding the various embodiments of the invention. When cover 250 is attached to roller 210, peaks 240 can be used as pressure points to apply alternating pressure to muscles and other tissue when roller 210 is rolled along a portion of a user's body. Roller 210 wrapped in cover 250 can be further used in conjunction with a cover similar to cover 50 of the embodiment in FIGS. 4-7. In this manner, ridges from cover 250 and thermal capacity from cover 50 can be added to a generally flat roller such as roller 210.

Figure 17:
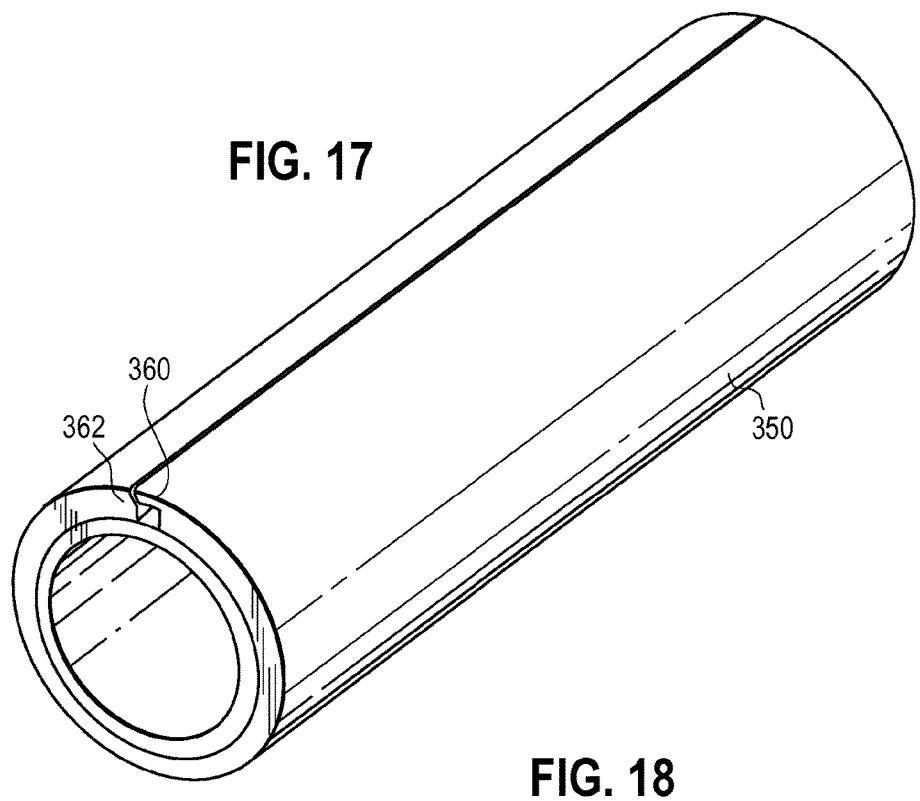
FIG. 17 is a perspective view of an alternative embodiment of a thermal cover attached to a massage roller of the present invention.

In an embodiment shown in FIG. 17, roller 210 is used in conjunction with alternative cover 350 having a flat surface on both sides of the cover. Cover 350 has complementary edges 360, 362 that interface with one another when cover 350 is wrapped around roller 210. Preferably, cover 350 includes an attachment mechanism located near complementary edges 360, 362 that allow the edges to be removably connected to one another.

The roller and various structures of the invention described herein can be constructed in a unitary nature from a single material. The invention can also be constructed from various different materials pieced together to create the structure or structures of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A massage therapy device comprising:
   a roller defining a substantially cylindrical base extending along a longitudinal axis between a first end and a second end;
   a ridge structure located on the cylindrical base between the first end and the second end, the ridge structure comprising two or more arms each originating and extending from a central area of the cylindrical base and each arm terminating at a distance from the first end and the second end;
   a detachable thermal cover comprising an attachment mechanism and defining a cavity containing thermal retention fill, the thermal cover surrounding at least a portion of the cylindrical base when attached to the base; and
   wherein the thermal retention fill retains thermal energy when heated or cooled.

2. The massage therapy device of claim 1 wherein the ridge structure comprises four arms each originating and extending from the central area of the cylindrical base and arranged in a generally X-shaped array.

3. The massage therapy device of claim 1 wherein the roller further comprises a first raised wheel-shaped disk extending from the cylindrical base adjacent the first end and a second raised wheel-shaped disk extending from the cylindrical base adjacent the second end, the first and second wheel-shaped disks having a common axis of rotation with the cylindrical base.

4. The massage therapy device of claim 3 wherein the first and second wheel-shaped disks have a thickness equal to one quarter of a diameter of the disks.

5. The massage therapy device of claim 1 wherein the thermal retention fill is selected from the group consisting of rice, seed, grain, corn, metal beads, plastic beads, gel, oil, water and a combination of two or more of the foregoing.

6. The massage therapy device of claim 1 wherein the attachment mechanism comprises a hook and loop fastener.

7. The massage therapy device of claim 1 wherein the roller comprises a foamed material selected from the group consisting of polyethylene, cross-linked polyethylene, polyurethane, reticulated polyurethane, polypropylene, polystyrene, polyvinylchloride, nylon, polycarbonate and a combination of two or more of the foregoing.

8. The massage therapy device of claim 1 wherein the roller comprises a rotationally molded material.

9. The massage therapy device of claim 1 wherein the roller comprises a machined material.

10. The massage therapy device of claim 1 further comprising a lobe formed by the two or more arms, wherein the lobe is a semi-circle structure and extends from a first side of the base cylinder to an opposite second side.

11. A cylindrical roller comprising:
    an elongate core member having a longitudinal axis and a first diameter and terminating in symmetric end portions each of which has a second diameter larger than the first diameter; and
    a plurality of lobes on the core member extending outwardly from the core member at an acute angle relative to the longitudinal axis of the core member, each lobe defining a massage plane with two or more lobes intersecting to form a valley and defining ribbon-like external contact surfaces around the periphery of the lobes.

12. The cylindrical roller device of claim 11 wherein a first lobe intersects with a second lobe to form an intersection angle between 150 degrees and 70 degrees.

13. The cylindrical roller device of claim 11 wherein the elongate core member and the plurality of lobes are unitary.

14. The cylindrical roller device of claim 11 wherein the elongate core member is tubular and defines a hollow interior cavity.

15. The cylindrical roller device of claim 11 further comprising a thermal cover detachably connected to the roller, the thermal cover defining a cavity containing thermal retention fill and further comprising one or more fasteners securing the cover over the elongate core.

16. The cylindrical roller device of claim 11 further comprising a thermal cover detachably connected to the roller comprised of a thermal retaining material selected from the group consisting of rubber, plastic, polymer and a combination of two or more of the foregoing.

17. A massage therapy device comprising:
    a roller comprising an elongate core member having a diameter and a longitudinal axis terminating at each end in a wheel-shaped disk of larger diameter than the diameter of the core member;
    a ridge structure located on the core member, the ridge structure comprising two or more arms each originating and extending from a central area of the core member, the two or more arms forming a first pair of opposed lobate structures, the first pair of opposed lobate structures extending outwardly from the core member and defining a massage plane comprising ribbon-like external contact surfaces around the periphery of the massage plane, wherein a first lobate structure intersects with a second lobate structure at an intersection angle of 140 degrees forming a valley;
a thermal cover comprising a hook and loop fastener and a sealed cavity containing corn, the thermal cover being removably attachable to the roller by wrapping the thermal cover around at least a portion of the cylindrical base and securing the hook and loop fastener; and
wherein the thermal retention fill is adapted to retain thermal energy when heated or cooled.

18. The massage therapy device of claim 17 wherein the roller has a length of 15 inches and the wheel-shaped disks have a diameter of 6 inches.

19. The massage therapy device of claim 17 wherein each lobate structure forms a semi-circular flat face having a length of 6 inches at its longest dimension.

20. The massage therapy device of claim 17 further comprising a second pair of opposed lobate structures extending outwardly from the core member and defining a second massage plane comprising ribbon-like external contact surfaces around the periphery of the second massage plane, wherein portions of the ribbon-like external contact surfaces of both the first pair and the second pair of lobate structures extend above the surface of the elongate core member to form a raised peak.

* * * * *